United States Patent
Al-Saggaf et al.

(10) Patent No.: US 11,559,232 B1
(45) Date of Patent: Jan. 24, 2023

(54) GRU BASED REAL-TIME MENTAL STRESS ASSESSMENT

(71) Applicant: King Abdulaziz University, Jeddah (SA)

(72) Inventors: Ubaid M. Al-Saggaf, Jeddah (SA); Muhammad Moinuddin, Jeddah (SA); Syed Saad Azhar Ali, Seri Iskandar (MY); Syed Faraz Naqvi, Seri Iskandar (MY); Sulhi Ali Alfakeh, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 17/681,790

(22) Filed: Feb. 27, 2022

(51) Int. Cl.
| | |
|---|---|
| A61B 5/16 | (2006.01) |
| A61B 5/374 | (2021.01) |
| A61B 5/00 | (2006.01) |
| A61B 5/384 | (2021.01) |
| G06N 3/08 | (2006.01) |
| G16H 50/20 | (2018.01) |

(52) U.S. Cl.
CPC .............. *A61B 5/165* (2013.01); *A61B 5/374* (2021.01); *A61B 5/384* (2021.01); *A61B 5/4836* (2013.01); *A61B 5/6801* (2013.01); *A61B 5/7264* (2013.01); *G06N 3/084* (2013.01); *G16H 50/20* (2018.01)

(58) Field of Classification Search
None
See application file for complete search history.

(56) References Cited

U.S. PATENT DOCUMENTS

| | | | |
|---|---|---|---|
| 11,179,089 B1 | 11/2021 | Al-Saggaf et al. | |
| 2001/0003145 A1* | 6/2001 | Mori | A61B 5/374 600/544 |
| 2013/0060125 A1* | 3/2013 | Zeman | A61B 5/374 600/409 |
| 2017/0147578 A1* | 5/2017 | Hecht | A61B 5/4064 |
| 2017/0311882 A1* | 11/2017 | Saab | A61B 5/4848 |
| 2019/0175091 A1* | 6/2019 | Das | A61B 5/165 |
| 2019/0216392 A1* | 7/2019 | Bower | G16H 30/40 |
| 2020/0000337 A1* | 1/2020 | Ducao | G16H 40/67 |
| 2020/0107766 A1* | 4/2020 | Liu | G16H 40/63 |
| 2020/0178888 A1* | 6/2020 | Nakae | G06K 9/00543 |
| 2021/0110895 A1 | 4/2021 | Shriberg et al. | |
| 2021/0353224 A1* | 11/2021 | Etkin | A61B 5/245 |

FOREIGN PATENT DOCUMENTS

CN 110135244 A * 8/2019 ......... G06K 9/00268

OTHER PUBLICATIONS

Machine Translated CN-110135244-A (Year: 2019).*
Al-Shormans "Frontal lobe real-time EEG analysis using machine learning techniques for mental stress detection" 2021.

(Continued)

*Primary Examiner* — Sean P Dougherty
*Assistant Examiner* — Benjamin S Melhus
(74) *Attorney, Agent, or Firm* — WCF IP

(57) ABSTRACT

Methods, systems and wearable devices for real-time mental stress assessment are provided. The methods and systems employ deep learning using a Gated Recurrent Unit (GRU) gating mechanism in a recurrent neural network with a sliding window approach applied to raw EEG data.

9 Claims, 7 Drawing Sheets

(56) References Cited

OTHER PUBLICATIONS

Can "Continuous Stress Detection Using Wearable Sensors in Real Life: Algorithmic Programming Contest Case Study" 2019.
Gedam "A Review on Mental Stress Detection Using Wearable Sensors and Machine Learning Techniques" 2021.
Navqi "Real-Time Stress Assessment Using Sliding Window Based Convolutional Neural Network" 2020.
Vanitha "Real time stress detection system based on EEG signals" 2016.

* cited by examiner

```
┌─────────────────────────┐
│      BLOCK ONE:         │
│ ACQUIRE RAW EEG SIGNALS IN │
│     SHORT WINDOWS       │
└─────────────────────────┘
```

```
┌─────────────────────────┐
│      BLOCK TWO:         │
│ FILTER AND TRANSFORM EEG │
│        SIGNALS          │
└─────────────────────────┘
```

```
┌─────────────────────────┐
│     BLOCK THREE:        │
│  EXTRACT AND CLASSIFY   │
│ TEMPORAL FEATURES WITH GRU │
│         UNITS           │
│                         │
└─────────────────────────┘
```

Figure 3

GRU BASED REAL-TIME MENTAL STRESS ASSESSMENT

BACKGROUND OF THE INVENTION

Technical Field

The invention generally relates to methods, systems and wearable devices for real-time mental stress assessment. In particular, the methods and systems employ deep learning using a Gated Recurrent Unit (GRU) gating mechanism in a recurrent neural network with a sliding window approach applied to Electroencephalogram (EEG) data.

Description of Related Art

Mental stress assessment is one of the most important steps for behavior evaluations. If mental stress is not diagnosed early and correctly treated, the condition can progress towards depression, anxiety, and in some cases, suicide attempts. A domain expert in psychoanalysis often relies on mental stress assessment that is based on feedback by the subjects to set questionnaires. However, these questionnaires are very subjective, and the analysis requires vast experience. Psychiatrists can also perform analyses on measured brain activities. There are many modalities by which mental stress can be assessed but EEG is one of the non-invasive techniques with a high temporal property. Evaluating EEG signals requires domain knowledge and experience, but even with the knowledge and experience, mental stress can still be misdiagnosed. This can be due to the subjective nature of assessment. To assist the psychiatrist, there are several machine learning-based approaches to assess mental stress. Some applications require time-efficient stress assessment in real-time, such as wearable devices and neurofeedback, where a decision may be needed within seconds. However, conventional machine learning algorithms are time consuming and require domain expertise in signal processing to extract the necessary features for classification. Therefore, a system is needed to extract the most significant features in real-time, especially for wearable devices. The system should also perform mental stress assessment in real-time with high accuracy and generalization so that its implementation can be possible for all participants or patients. A system and method providing a combination of such solutions can also solve the mobility problem of current devices so that wearable devices can be developed.

Another issue with conventional approaches is the use of batch data for assessment. The general flow of such an approach is diagrammed in FIG. 1 and includes raw EEG signal acquisition 10; preprocessing 20 of data; multi-signal filtration 30; feature extraction 40; and classification 50.

A conventional machine learning system's use of batch data (including batching of samples for training the classifier) is an indicator that the system may be unsatisfactory for real-time applications. To assess batch size data, conventional systems consume a significant time, and to recording such large amounts of data, the participant must wait for a long period of time. Such conditions do not meet requirements of real-time systems.

Issued U.S. Pat. No. 11,179,089 ("the '089 patent") discloses a real-time intelligent mental stress assessment system and method for wearable devices. The '089 patent method includes acquiring, by EEG sensors, an EEG signal; obtaining alpha, beta, and theta frequency bands from the EEG signal; extracting features of the alpha, beta, and theta frequency bands with processing circuitry having a machine learning model and classifying the features of the alpha, beta, and theta frequency bands to obtain a classification result of mental stress or no mental stress. However, the '089 patent machine learning model does not use GRU to perform the extraction and classification but rather a first bidirectional long short-term memory (LSTM) layer and a second bidirectional LSTM layer, wherein the extracting is performed with the first bidirectional LSTM layer and the classifying is performed with the second bidirectional LSTM layer.

US patent application 20210110895 ("the '895 reference") discloses systems and methods for assessing a mental state of a subject using queries to which the subject responds. The queries, which may be audio, visual, or textual, may be based in part on one or more target mental states to be assessed. However, the method disclosed in the '095 reference does not receive or process EEG data.

Can et al (2019) discloses wearable sensors for a real-time stress assessment using physiological parameters (heart activity, skin conductance and accelerometer signals) not EEGs, and GRUs are not mentioned.

Naqvi et al. (2020) discloses a real-time mental stress assessment technique employing convolutional neural networks (CNNs) and unsupervised data extraction and classification. This system uses a small "sliding windows" (40 ms) for data acquisition from EEGs but the data is not processed using GRUs.

Vanitha (2016) describes techniques using EEG as a tool to measure stress. However, the EEG signal is pre-processed to remove artifacts and relevant time-frequency features are extracted using Hilbert-Huang Transform (HHT). The extracted features are manipulated to detect stress levels using hierarchical Support Vector Machine (SVM) classifier. GRUs are not mentioned.

Gedam and Paul (2021) a review of mental stress detection using wearable sensors and machine learning techniques. One section is devoted to a discussion of sensors using EEG data (beginning on page 84056 and see Table 9). GRU is not discussed as a possible machine learning approach to data analysis.

Al Shorman (2021) teaches frontal lobes EEG spectrum analysis to detect mental stress. A Fast Fourier Transform (FFT) is used as a feature extraction stage to measure all bands' power density for the frontal lobe. Two types of classifications are used such as subject wise and mix (mental stress vs. control) using Support Vector Machine (SVM) and Naïve Bayes (NB) machine learning classifiers. However, GRU extraction and classification is not used or mentioned.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

A deep learning approach for mental stress assessment in real-time is provided. The approach utilizes a Gated Recurrent Unit (GRU) gating mechanism in a recurrent neural network with a sliding window approach applied to raw EEG data. The method avoids conventional pre-processing and data cleansing processes and instead uses an intelligent approach to extract the most significant features and neglect others that do not contribute to discriminating patterns between stressful and non-stressful EEG signals. This increases the overall quality of the features and influences the performance of the "stress" or "no stress" classification. Because the response time of the process is rapid, the whole algorithm assesses mental stress in significantly reduced time. The method is thus time-efficient and is a suitable for use in wearable devices for real-time applications.

It is an object of this disclosure to provide a method of classifying electroencephalograph (EEG) signals from a subject as indicative of the subject being in a state of mental stress or a state of no mental stress, comprising acquiring short windows of raw EEG signals from the subject;

filtering the short windows of raw EEG signals to remove delta and gamma bands and retain alpha, beta, and theta signals, to produce filtered EEG signals;

performing a classifying, by a deep learning convolutional neural network (DLCNN) comprising gated recurring units (GRUs), which comprises:
 i) extracting temporal features of the filtered EEG signals, and
 ii) classifying the temporal features to obtain a classification result of mental stress or no mental stress.

In some aspects, the DLCNN comprises at least one input layer, at least one fully connected pooling layer, and at least one layer comprising GRUs, wherein each layer comprising GRUs is located between an input layer and a fully connected layer.

In further aspects, the acquiring short windows of raw EEG signals comprises a receiving, by a microcontroller that includes processing circuitry, which is secured to a wearable device that is worn by the subject, of raw EEG signals obtained from the subject by an EEG sensor that is secured to the wearable device, or to another wearable device that is worn by the user, and the extracting and the classifying are performed in real-time by the processing circuitry of the microcontroller.

In additional aspects, the extracting and classifying are performed in real-time by processing circuitry embedded in a mobile device.

In yet further aspects, the method further comprises displaying, by a display device, one or both of the EEG signals and the classification result.

In yet additional aspects, the method further comprises when the subject is in a state of mental stress, providing an anti-stress therapy to the subject.

The present disclosure also provides a method of assessing mental stress in real time in a subject in need thereof, comprising: filtering the raw EEG signals to remove delta and gamma bands and retain alpha, beta, and theta signals, to produce filtered EEG signals; transforming the filtered EEG signals into windows; performing a classifying, by a deep learning convolutional neural network (DLCNN) comprising gated recurring units (GRUs), the classifying comprising: i) extracting temporal features of the filtered EEG signals, and ii) classifying the temporal features to obtain a classification result of mental stress or no mental stress; and outputting a classification result in real time. In some aspects, the windows are less than 1 second. In other aspects, the windows are less than 200 milliseconds. In further aspects, the windows are 40 milliseconds. In additional aspects, the method further comprises when a classification result of mental stress is obtained, providing the subject with a therapy to decrease mental stress.

The present disclosure also provides a wearable device comprising processing circuitry configured to perform a method of assessing mental stress in real time in a subject in need thereof, comprising: filtering the raw EEG signals to remove delta and gamma bands and retain alpha, beta, and theta signals, to produce filtered EEG signals; transforming the filtered EEG signals into windows; performing a classifying, by a deep learning convolutional neural network (DLCNN) comprising gated recurring units (GRUs), the classifying comprising: i) extracting temporal features of the filtered EEG signals, and ii) classifying the temporal features to obtain a classification result of mental stress or no mental stress; and outputting a classification result in real time.

BRIEF DESCRIPTION OF THE DRAWINGS

FIG. 3. Schematic depiction of the first, second and third blocks of the method.

DETAILED DESCRIPTION

Figure 1:
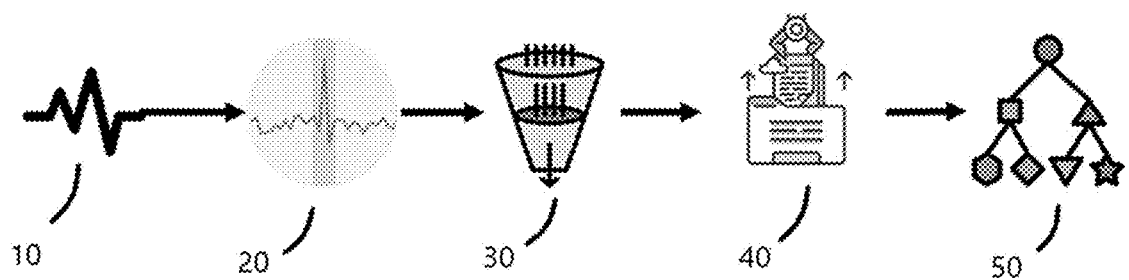
FIG. 1. General prior art machine learning-based classification approach. 10 represents EEG data; 20 represents pre-processing; 30 represents multi-signal filtration; 40 represents feature extraction; and 50 represents classification of features.

Aspects of this disclosure are directed to a system, device (such as a mobile or wearable device), and method for performing mental stress assessment in real-time with high accuracy and generalization. The system, device, and method extract the most significant features related to mental stress in real-time. In some aspects, the features are extracted from signals that are obtained using wearable devices.

The quality of input features greatly influences the performance of a computerized, deep learning data classifier. When the response time of the classification process is rapid, the whole algorithm has the capability to assess mental stress in significantly less time. To accomplish rapid classification, the feature extraction step(s) for machine learning need(s) pre-processed data that are clean from abnormal signal data, e.g. artifacts or noise. However, artifact and noise removal adds time to the whole process. Considering real-time stress assessment algorithm requirements, what is needed is a method that automatically extracts features from raw EEG data and classifies the data from subjects as stressed or non-stressed using an algorithm that is both time-efficient and accurate.

Embodiments provide, among other features and benefits, a solution to the time and computation costs of pre-processing, by using raw neuronal EEG signals for mental stress assessment. Embodiments' removal of the pre-processing required by conventional techniques assists in providing real-time, time-efficient, and accurate deep learning assessment of mental stress assessment using raw EEG data. Embodiment features that remove the conventional techniques' need for pre-processing and its associated burden include, a gated recurrent unit (GRU) based deep learning. In arrangements and combination in accordance with disclosed embodiments, GRUs are components of particular recurrent neural network that uses connections through a sequence of nodes to perform machine learning tasks. The GRUs, in accordance with disclosed embodiments, extract the more significant features upfront and neglect ones that do not contribute to the ability to discriminate patterns between stressful and non-stressful EEG signals. During unsupervised training operations of extracting of features, GRUs in systems and methods according to disclosed embodiments also reduce abnormalities and noise from the EEG signals. This provides at least, and potentially more of the increase in training efficiency and quality as obtained from conventional techniques' pre-processing, without the costs.

Embodiments provide, among other features, the use of smaller windows for classification. This provides, among other benefits, high data resolution, which is among the empirical properties because it allows extracting significant features that are not biased or affected by other factors.

The present methods advantageously decrease the computation time of the entire process compared to conventional processes which can be tedious, lengthy, and sensitive towards abnormalities and error.

Gated Recurrent Units (GRUs)

GRUs are gating mechanisms in recurrent neural networks introduced in 2014 by Kyunghyun Cho. GRUs have fewer parameters than, for example, LSTMs, and omit an output gate.

As part of a specific model of recurrent neural network, a GRU uses connections through a sequence of nodes to perform machine learning tasks associated with memory and clustering. GRUs help to adjust neural network input weights to solve the vanishing gradient problem that is a common issue with recurrent neural networks.

As a refinement of the general recurrent neural network structure, GRUs have an update gate and a reset gate. The update gate and the reset gate can be referred to as vector entries. Using these two-vector entries, the model refines outputs by controlling the flow of information through the model. Like other kinds of recurrent network models, models with GRUs can retain information over a period of time, i.e., the models are a "memory-centered" type of neural network that results in machine "learning".

Methods and Systems According to Disclosed Embodiments

Figure 2:
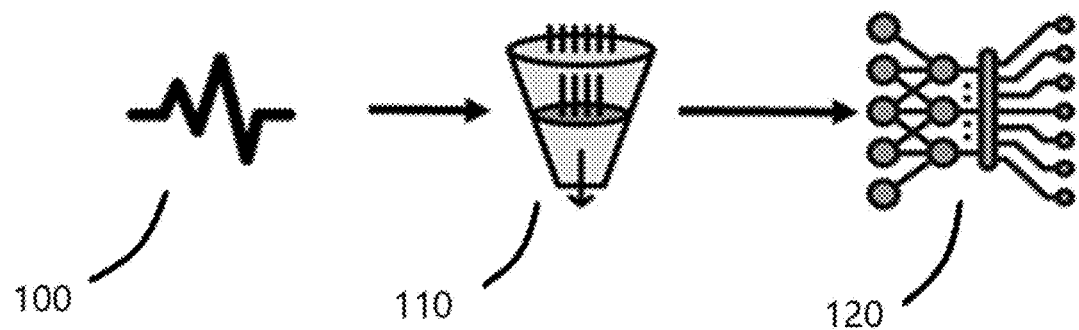
FIG. 2. General deep learning-based classification approach of the present invention. The approach does not require pre-processing, multiple band extraction, and supervised feature extraction. 100 represents EEG data; 110 represents single signal filtration; and 120 represents deep learning (DL) classification of features.

FIG. 2 shows a logic flow diagram of example operations 200 in a process in accordance with one or more embodiments. The FIG. 2 process, as diagrammed, comprises raw EEG signal acquisition 202; single signal filtration (band extraction) 204; and deep learning (DL) classification 206 based on extracted features. As will be appreciated by persons of ordinary skill in the relevant art upon reading this disclosure, practices in accordance with disclosed embodiments reduces computation resource requirements, and reduces computation time compared to convention techniques, The system tasks can be divided into three blocks, such as illustrated in FIG. 3.

First Process Block: Raw EEG Signal Acquisition 302

Raw EEG signal acquisition 302 acquires EEG signals from regions having relevance to mental stress assessment. Means for such acquisition can include electrodes attached to the scalp of a subject using the device described herein. Each electrode can connect to one input of a differential amplifier; a common system reference electrode is generally connected to the other input of each differential amplifier. The amplifiers amplify the voltage between the active electrode and the reference (typically from about 1,000-100,000 times, or from about 60-100 dB of voltage gain). In analog EEG device, the signal is filtered, and an analog EEG signal is output. In a digital EEG device, the amplified signal is digitized via an analog-to-digital (A/D) converter, after being passed through an anti-aliasing filter. A/D sampling rate can be, for example and without limitation from 256 to 512 Hz. Other sampling rates may be used, such as but not limited to, up to 20 kHz. A digital EEG device may have a bit resolution of, e.g., 12, 15, or 24 bits.

According to various embodiments assessment of EEG signals from a subject in real-time may use a sliding window approach. To render EEG signals compatible for the sliding window, in addition to selecting only alpha, beta, and theta bands, the EEG signals can be divided into shorter windows to extract the features having more significance to discriminating stress and non-stress signals. The feature selection and shorter window provide, for example reduction in the wait time for the participant/subject compared to that experienced in conventional approaches. The short windows may be fixed-length windows of a length that, for example, may be preferably less than one second, or even less than 50 milliseconds. A minimum length of the windows can be, for example, approximately 20 milliseconds, to ensure an adequate signal for classification of mental stress assessment. According to an embodiment, the window size may be set to, for example, approximately 40 milliseconds.

Second Process Block: Band Extraction (Single Signal Filtration) and Transformation 304

According to various embodiments, a band extraction (single signal filtration) and transformation 304 process can include receiving EEG signals that may contain artifacts and/or distortions. In conventional deep learning EEG classification systems and methods, signals containing distortion or artifacts can negatively affect both the deep learning process, and subsequent classification using the classifier that results from the training. Negative effect can include, for example, bias in the training result, i.e., a biased classifier. Noise and artifacts in EEG data obtained for subsequent classification processes using the trained classifier can cause, for example, miss-classification. Therefore, it can be preferable to filter or clean the EEG signals, prior to feature extraction. If features extracted from uncleaned EEG signals are used in the deep learning process, resulting learning models may become overfit, under-fit, or give a bad classification performance.

Systems and methods according to various embodiments provide, among other features and benefits, a novel and effective band extraction that, for example and without limitation, reduces the overall time consumption for extracting bands and is compatible with the learning model. In one or embodiments, a particularly configured band extraction module can be included and, as described in more detail in later section of this disclosure, can provide, without limitation, a specific range of bands to the GRU module for classification.

Conventional EEG approaches can include different band extraction filters to isolate different frequency bands from EEG signals, namely, alpha, beta, theta, gamma, delta. Computation costs of such approaches can render real-time assessment economically infeasible for practical applications. Systems and methods according to various embodiments overcome these shortcomings by, for example and without limitation, utilizing the more significant bands while ignoring other bands. In one or more embodiments, alpha, beta, and theta bands are utilized, while delta and gamma are removed from the raw EEG signals and not utilized. In other words, the bands that were found to be insignificant or less efficient for the accuracy of the model are removed. In an embodiment, this includes the delta and gamma bands.

Third Process Block: Classification

An important block for classification is the choice of the model that is used for discriminating EEG features (passed from the second block) into given classes. The classification block receives the filtered EEG signals transformed into the required format as described above.

In accordance with various embodiments, classification can be based on GRUs and on combinations and arrangements of GRUs. They are responsible for extracting significant features and estimating the final output. GRUs are designed to assess features based on their temporal relationship, i.e. the GRUs are responsible for extracting temporal information.

Figure 4A:
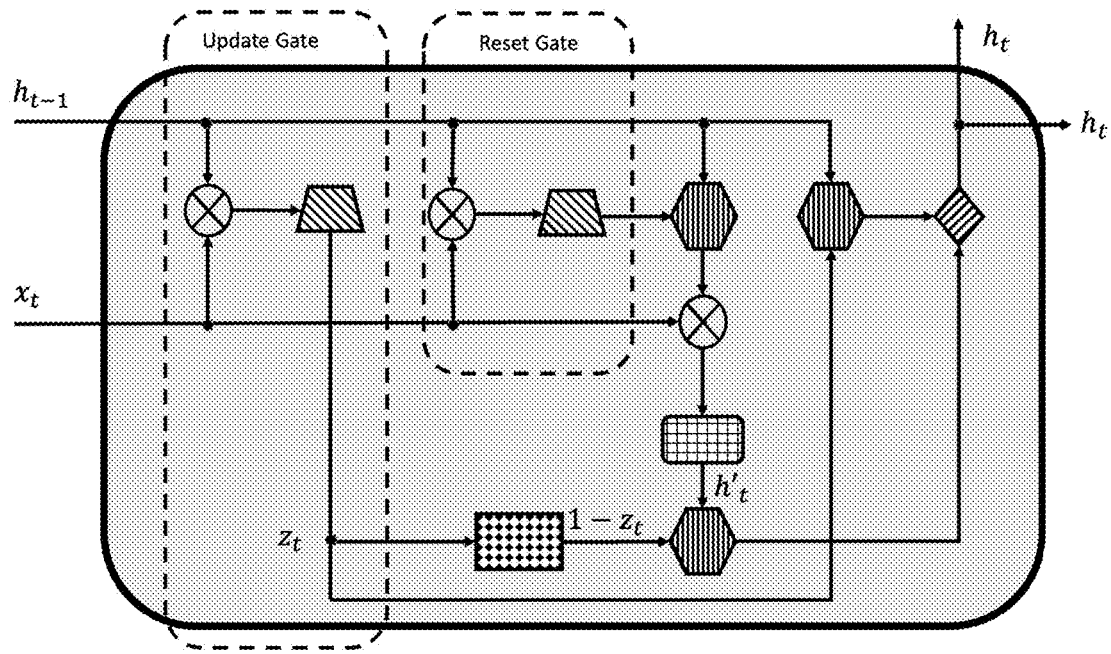
FIG. 4A and B. Schematic depictions of gates within a GRU unit. A, GRU showing update and reset gates; B, GRU showing vectors and operational functions.

As described above, internal structure of GRUs can be described as working according to a gate system. In GRUs, there can be two main gates and two states: the two main gates can comprise, as also described above, an update gate and a reset gate, as illustrated in FIG. 4A. The two gates can provide a current memory state and a final memory state. The main gates can be considered as two vector entries (0,1) that perform a convex combination. These combinations can decide which hidden state (memory) information should be updated (passed) and/or reset the hidden state whenever needed. Likewise, the network learns to skip irrelevant temporary observations.

Update Gate:

The update gate is an updated form of a forget gate. Another functionality of the update gate is letting information from the previous layer into the current layer. In the update gate, an activation function, e.g. a Sigmoid activation function, compresses the values to between 0-1, where 0 represents erasing any information from the previous unit, and 1 triggers the unit to keep the information from the previous GRU.

Reset Gate:

The reset gate is used to decide whether the model should learn from the previous unit or not, i.e. how much of the past information to forget. The reset gate has some similarity to the update gate, as it receives data from the previous unit and current memory unit and utilizes, e.g. a Sigmoid activation function, but the data is fed into different places for different purposes. The reset gate is used to set the current memory unit (state).

Current Memory State:

The current memory state is derived from the reset gate, and it keeps account of the information that should be passed to the final memory state of the unit. The current memory state is responsible for dealing with the conditions in which data from the previous unit should be retained or removed before sending its product to the final memory state. It can use the Tanh function as an activation function to compress data to values between −1 and +1, which can differ from the previous gates' using of conventional Sigmoid functions.

Final Memory State:

What may be last step of the GRU unit is to hold the current memory location and then pass it down the network. For this purpose, the update gate and the current memory state can determine which data should be retained and transferred to the next GRU unit. This step adds data element-wise, and activation functions are not required.

Figure 4B:
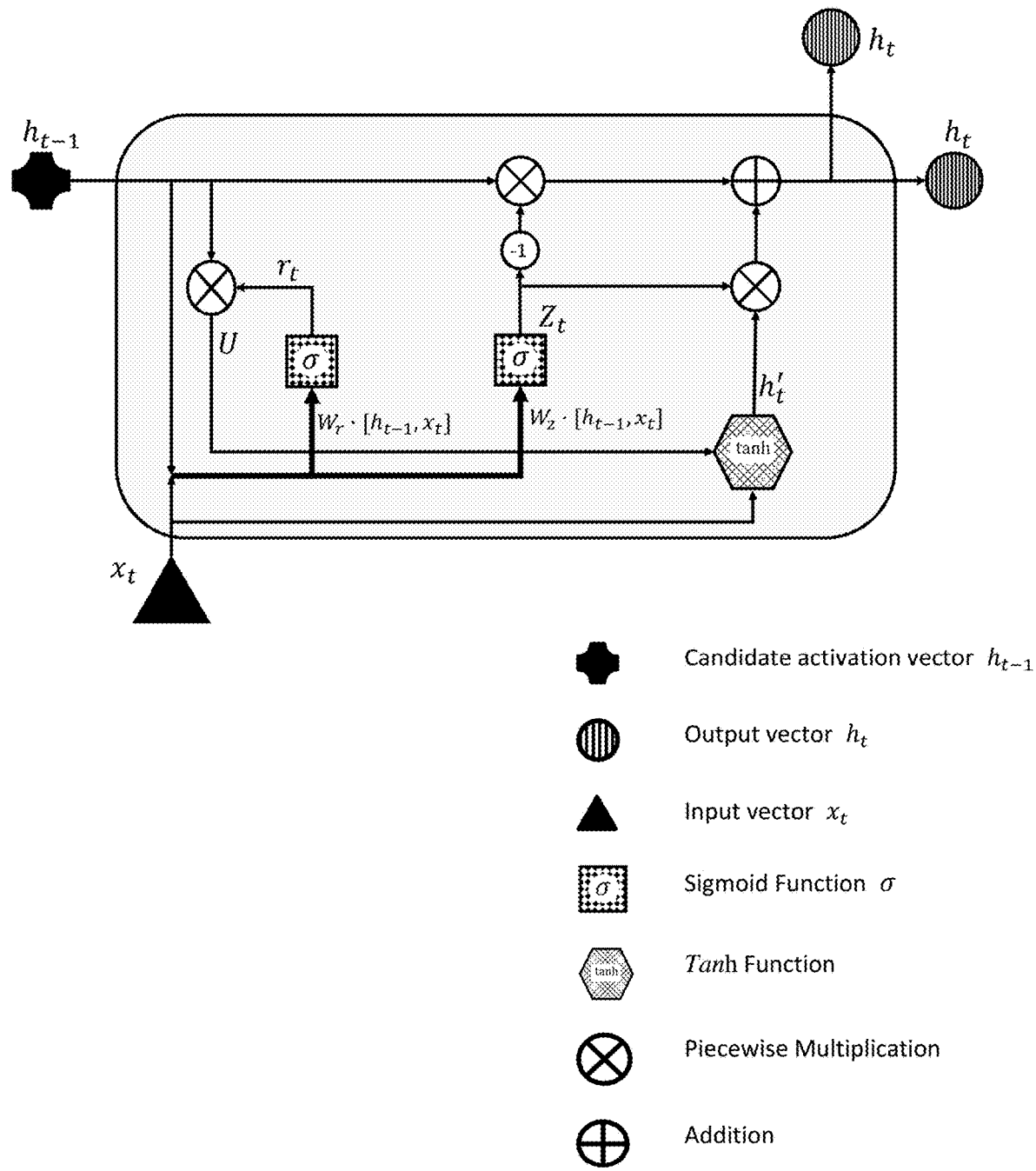

Further details of the operations in a GRU are illustrated in FIG. 4B.

Figure 5:
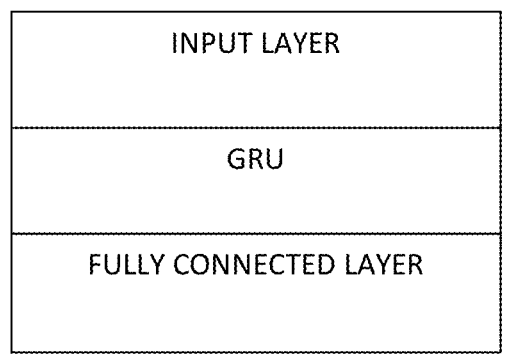
FIG. 5. Schematic depiction of a gated recurrent unit (GRU) located (positioned) between an input layer and a fully connected layer.

FIG. 5 illustrates the feature that each GRU is typically located (positioned) between an input layer and a fully connected layer.

Figure 6:
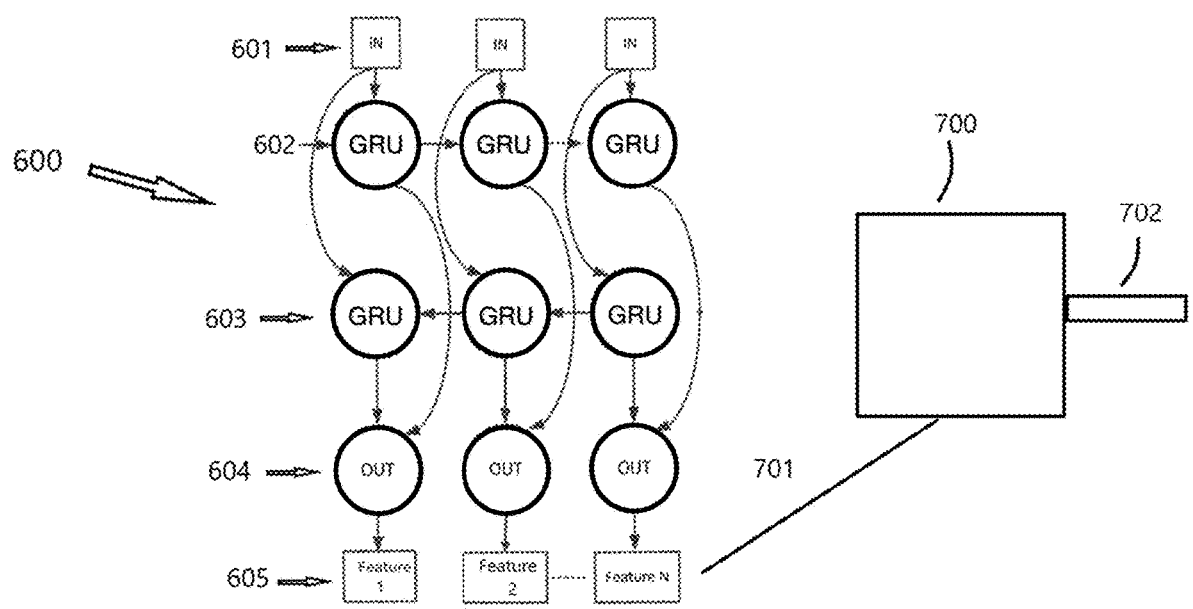
FIG. 6 is a block diagram of a Bidirectional GRU.

FIG. 6 is a diagram of a Bidirectional GRU according to various embodiments for unsupervised feature extraction. The Bidirectional GRU 600 can perform signal propagation both backward and forward in time. The input vector 601 is a window of a EEG signal, for example a signal of length 40 milliseconds. The window of the EEG signal propagates both forward through GRU units 602 and propagates backward through GRU units 603. The number of GRU units in the forward and the backward flow is based on the length of the window. Although the GRU of FIG. 6 shows two Bidirectional layers, the number of layers can be varied. An output layer 604 outputs significant features 605 of the signal. Each of the significant features 605 may be in the form of scores or probabilities (likelihoods). The feature set comprises abstract values that are based on the weights determined during the learning phase.

A Bidirectional GRU layer 700 is used for classification of the EEG window 601, taking as input 701 the extracted features. The structure of Bidirectional GRU layer may be similar to the structure of layer 601. The Bidirectional GRU also propagates forward through GRU units as well as backward through GRU units and includes one or more output neurons 702 that output a classification, as either mental stress or not mental stress related. The output classification may be in the form of a score or probability (likelihood) of the classification that is output to e.g. a mobile device such as described below.

Devices and Systems

Systems and methods according to disclosed embedment can, among other features and benefits, enable conserving the temporal information within EEG signals and extracting significant hidden information between these temporal associations in order to classify the signals as indicating stress or no stress. Systems and methods according to disclosed embodiments can also provide, for example and without limitation, required classification in a substantially reduced amount of time, making it compatible with real-time stress assessment. Embodiments can further enable, e.g., via computational speed and efficiency, assessment using and compatible with wearable devices.

Figure 7:
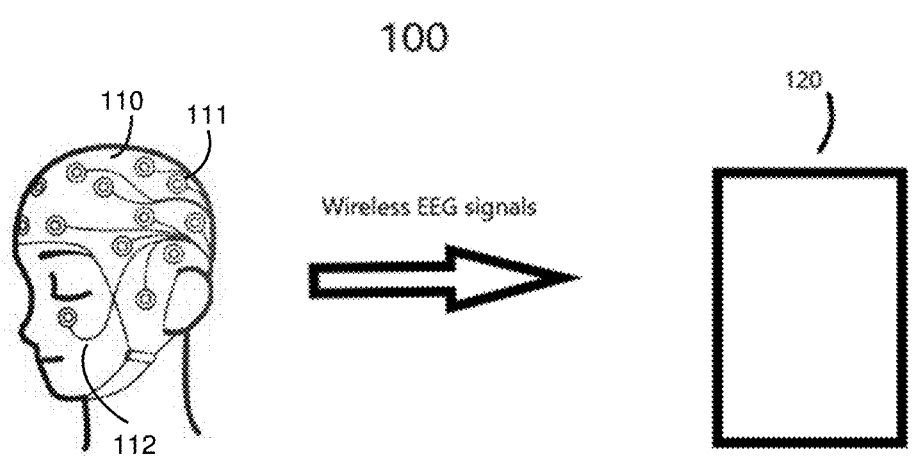
FIG. 7. Schematic depiction of a device of the invention and method of its operation.

FIG. 7 is a schematic diagram of an exemplary mobile, wearable system for mental stress assessment in accordance with various embodiments. The system 100 can include a headset 110 that can be in wireless communication (represented by the arrow) with a device 120. The device 120 can comprise a data processing device, e.g., a data processor coupled to memory storing, as software programming, executable instructions for performing one or method in accordance with disclosed embodiments, to assess stress as described herein, e.g. a stress assessment mobile application such as an "App". The headset 110 is used to obtain EEG signals from the person wearing the headset 110. EEG is an electrophysiological monitoring method to record electrical activity on the scalp that has been shown to represent the macroscopic activity of the surface layer of the brain underneath. It is typically non-invasive, with the electrodes placed along the scalp. The wireless communications can be, for example a direct communication link, such as Bluetooth, or Bluetooth Low Energy (BLE), or can be performed over a wireless communication network, such as WiFi. In some aspects, a wireless communication is used to transmit the EEG signals to device 120. The device 120 and/or the App can display the results as, e.g. a graph or other visualization of received EEG band signals related to mental stress; results of mental stress assessment in terms of, for example, 'Stressed' and 'Not Stressed"; duration in terms of % of the session time where the subject was under stress; etc.

EEG systems, such as wearable EEG device 110, uses electrodes 111, each of which is attached to an individual wire 112. In some embodiments, the wearable EEG device 110 may be or include a cap or net into which electrodes are embedded. In most clinical applications, a plurality (e.g. from about integer 5 to about integer 25, such as about 5, 6, 7, 8, 9, 10, 11, 12, 13, 14, 15, 16, 17, 18 19, 20, 21, 22, 23, 24, or 25, e.g. about 19, recording electrodes (plus ground and system reference) are used. A smaller number of electrodes can be used when recording EEG from neonates. Additional electrodes can be added to the standard set-up when a clinical or research application demands increased spatial resolution for a particular area of the brain. High-density arrays (typically via cap or net) can contain up to integer 256 electrodes more-or-less evenly spaced around the scalp. For example, about integer 25 to 50, or 50 to 100, or 100 to 150, or 150 to 200, or 200 to 250, or 250 to 300 electrodes may be used (including all whole integers between these values).

A wearable EEG device 110 may have electrodes 111 that can be, for example, a flexible electrode arrangement, or rigid electrode arrangement, or combination of the two. The electrodes 111 may be thin wired elements that can be flexibly arranged on the scalp, and mounted to the scalp via adhesive, or may be rigid wired structures that substantially stay in a fixed arrangement. In a rigid wired structure, the electrodes 111 may form a tree-like arrangement that spreads out over an area of the scalp.

In some embodiments, the wearable EEG device 110 may include one or more support members (not shown). The wearable EEG device 110 may be a headband-type that includes a main C-shaped or oval-shaped support member that in itself contains the electrodes 111. The electrodes 111 may protrude from a surface of the support member or may be mounted to a surface of the support member. The wearable EEG device 110 may include additional support members having ends that connect to the main support member. The additional support members may be semicircular bands that loop over the scalp so that electrodes 112 may be positioned at other areas of the scalp.

Sensor electrodes 111 may be in the shape of a cup, disc, needle, etc. Sensor electrodes 111 may be wet or dry, in which wet electrodes 111 (e.g., felt pads) require application of a saline solution. EEG sensor electrodes 111 may obtain signals over one or more channels.

The wearable EEG device 110 may include other types of sensors, such as motion sensors (e.g. an inertial measurement unit (IMU)) to measure head movement, and temperature sensors. In addition, the system for mental stress assessment 100 may obtain optional sensor data from other sensors for an individual, such as a blood pressure measurement device, a heart rate detection device, a blood sugar monitoring probe, a blood oxygen level measurement device, to name a few. Such other sensor data may be used to determine the individual's physical condition during monitoring by the wearable EEG device 110.

The device may include a module for low energy short range communication, such as Bluetooth or BLE. The communication device may include a module for wireless communication, such as WiFi. The module for low energy short range communication may be used for communication with device 120, which may be a mobile device. The module for wireless communication may be used for communication with a wireless device connection.

Also provided are computer-readable media on which the instructions of the present processes are stored. For example, the instructions may be stored in FLASH memory, Secure Digital Random Access Memory (SDRAM), Random Access Memory (RAM), Read Only Memory (ROM), Programmable Read-Only Memory (PROM), Erasable Programmable Read-Only Memory (EPROM), Electrically Erasable Programmable Read Only Memory (EEPROM), solid-state hard disk or any other information processing device with which the processing circuit communicates, such as a server or computer.

Further, the advancements may be provided as a utility application, background daemon, or component of an operating system, or combination thereof, executing in conjunction with MPU 300 and a mobile operating system such as Android, Microsoft™ Windows™ 10 Mobile, Apple iOS™ and other systems known to those skilled in the art.

The requisite hardware elements may be implemented by various circuitry elements known to those skilled in the art. For example, MPU 300 may be a Qualcomm mobile processor, a Nvidia mobile processor, an Atom™ processor from Intel Corporation of America, a Samsung mobile processor, or an Apple A7 mobile processor, or may be other processor types that would be recognized by one of ordinary skill in the art. Alternatively, the MPU 300 may be implemented on an Field-Programmable Gate Array (FPGA), Application Specific Integrated Circuit (ASIC), Programmable Logic Device (PLD) or using discrete logic circuits, as one of ordinary skill in the art would recognize. Further, MPU 300 may be implemented as multiple processors cooperatively working in parallel to perform the instructions of the inventive processes described above.

Other elements of the system may optionally include a network controller, such as an Intel Ethernet PRO network interface card from Intel Corporation of America, for interfacing with a network. As can be appreciated, the network can be a public network, such as the Internet, or a private network such as LAN or WAN network, or any combination thereof and can also include PSTN or ISDN sub-networks. The network can also be wired, such as an Ethernet network. The processing circuit may include various types of communications processors for wireless communications including 3G, 4G and 5G wireless modems, WiFi™ Bluetooth™, GPS, or any other wireless form of communication that is known.

A display controller, such as a NVIDIA™ GeForce™ GTX or Quadro™ graphics adaptor from NVIDIA Corporation of America, may be included for interfacing with a display of the classification results. An I/O interface may interface with e.g. volume control, a microphone, one or more cameras, an audio input or output circuit, etc. The classification results may be output to a screen that is a touch screen, various support elements of which may include Industry Standard Architecture (ISA), Extended Industry Standard Architecture (EISA), Video Electronics Standards Association (VESA), Peripheral Component Interface (PCI), or similar, for interconnecting all of the system.

Methods

Provided herein are methods of classifying electroencephalograph (EEG) signals from a subject as indicative of the subject being in a state of mental stress or a state of no mental stress. Generally, the methods comprise steps of acquiring short windows of raw EEG signals from the subject; filtering the short windows of raw EEG signals to remove delta and gamma bands and retain alpha, beta, and theta signals, to produce filtered EEG signals; and then, using a deep learning convolutional neural network (DLCNN) comprising gated recurring units (GRUs): i) extracting temporal features of the filtered EEG signals, and ii) classifying the temporal features to obtain a classification result of mental stress or no mental stress. The invention advantageously provides e.g. mobile and/or wearable devices that perform the methods in real time. In some aspects, the output of the classifying step is displayed on a screen, e.g. of a mobile phone. This enables the user and/or health professionals working with the user to be aware of when the user is under stress, especially negative stress, and permits the user to adapt his or her behavior to reduce stress. For example, long hours of staying immobile in front of a computer screen while attempting to complete a task with a deadline may cause unhealthy stress. The present devices may alert a user to this stress and the user may decide to "take a break". Alternatively, the device may be used (periodically) to monitor the progress of a user who is learning to meditate, relax, etc., and or for desensitization to stressful situations such as interactions with specific individuals, and/or to overcome irrational fears or past traumas.

In some aspects, the output is a classification of "stress" or "no stress". The output may be provided to the user in any of a variety of forms, e.g. an audible signal (e.g. an audible signal is heard when stress is experienced), a color coded image (e.g. green is no stress, red is stress), etc. In addition, nuances may also be classified. For example, various degrees of stress (e.g. low stress, medium and high stress) may be identified using the devices and methods described herein.

Further, when a condition of mental stress is identified, the system may automatically provide therapeutic input (treatment, such as anti-stress treatment/therapy) to the user, e.g. soothing music, the sound of running water, a guided meditation, a prayer that is meaningful to the user, a depiction of a quiet pastoral scene, peaceful pictures of animals, etc. The input is provided in an amount that is effective to lessen or decrease stress. In other words, the user can be provided or treated with one or more of many different types of visual and/or audio feedback which can mitigate (decrease, lessen) mental stress and/or promote a feeling of well-being and low or no stress. The change to a "low" or "no stress" state can be monitored using the methods and apparatuses described herein. In some aspects, a subject classified as having stress or being in a state of mental stress may be treated with a therapeutically effective amount of an anti-anxiety and/or anti-depressant medication and/or may be treated with a therapeutically effective amount of behavioral therapy, talk therapy, psychoanalysis, etc. In addition, the present methods can be used to monitor the efficacy of such treatments and/or to adjust such treatments. For example, the frequency or duration of a treatment may be increased if the subject is identified as having the same amount or more stress when tested after a therapy has been provided (i.e. the treatment has not worked). Conversely, the frequency of a treatment may be decreased or even stopped if the subject is identified as having less or no stress when tested after a therapy is provided (i.e the treatment has been successful). This is especially useful when the methods are used for ongoing monitoring of the subject's stress level.

There are several types of medications used to treat anxiety disorders characterized by high levels of stress. Examples include but are not limited to: antidepressants including selective serotonin reuptake inhibitors (SSRIs), serotonin-norepinephrine reuptake inhibitors (SNRIs), tricyclic antidepressants (TCAs), monoamine oxidase inhibitors (MAOIs), tetracyclic antidepressants (TeCAs), or adrenergic and specific serotonergic antidepressant (NaSSAs); benzodiazepines such as alprazolam (Xanax), clonazepam (Klonopin), chlordiazepoxide (Librium), diazepam (Valium), and lorazepam (Ativan); buspirone; hydroxyzine; and beta-blockers such as acebutolol (Sectral), bisoprolol (Zebeta), carvedilol (Coreg), propranolol (Inderal), atenolol (Tenormin) and metoprolol (Lopressor).

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

For real-time stress assessment algorithm requirements, desired features include automatic extraction of features from raw EEG data and classification of the data in real time, between stressed and non-stressed subjects. Present embodiments exploit and uniquely leverage deep learning techniques using, for example, and the gated recurrent unit (GRU) based deep learning algorithm. A GRU is part of a specific model of recurrent neural network that uses connections through a sequence of nodes to perform machine learning tasks.

Short-windowed EEG signals were used for the assessment of mental stress in real-time. GRU (Gated Recurrent Units) were used for the classification of the short EEG windows.

As shown in Table 1 below, the model was compared with a machine learning (ML) approach that included feature extraction. The features used for the ML approach included coherence, energy, alpha-asymmetry, relative energy, and ratios. Logistic regression, SVM, and decision trees were used to train the extracted features and analyze accuracy and time consumption.

The ML approach was also compared with deep learning models. GRU was used for classification, and it outperformed the ML approach in terms of accuracy and time consumption/response. GRU was also compared with CNN and LSTM that belong to the same class of deep learning, but GRU also outperformed these algorithms based on the time responses.

Another criterion to evaluate the models is computation time; GRU is greatly compatible and lightweight compared to other deep and machine learning models and can also perform assessment in real-time, i.e., within 0.09 s. On the other hand, long short-term memory (LSTM), convolutional neural network (CNN), logistic regression (LR), support vector machine (SVM), and Decision tree (D-Tree) consumed 0.12 s, 0.65 s, 6.5 s, 6.5 s, and 4.4 s, respectively. Table 1 shows comparative results.

Table 1: Comparison of the Present Method with State-of-Art Techniques in Terms of Accuracy, Sensitivity, Specificity, and Computation Time

| Performance | Techniques | | | | | |
| --- | --- | --- | --- | --- | --- | --- |
|  | LR | SVM | D-Tree | CNN | LSTM | GRU |
| Accuracy | 57% | 84% | 84% | 96% | 98% | 98.5% |
| Sensitivity | 64% | 78% | 91% | 95% | 100% | 98% |
| Specificity | 48% | 90% | 71% | 97% | 96% | 99% |
| Computation Time (1 s data window) | 6.50 s | 6.87 s | 4.41 s | 0.65 s | 0.12 s | 0.09 s |

CONCLUSION

Methods according to disclosed embodiments can perform for example, mental stress assessment in real-time using raw EEG signals with low complexity and with high accuracy, high sensitivity and specificity, and with low computation time. This makes an especially advantageous approach for wearable devices.

Further advantages of the systems and methods according to disclosed embodiment include, but are not limited to:

Extracting of features automatically in an unsupervised manner

Conservation of temporal information within the EEG signals and extracting of significant hidden information between temporal associations.

Utilization, e.g., via a band extraction module, of specific range of bands or ranges of bands (Alpha, Beta, and Theta bands), and provision of the specific ranges to the GRU model for classification.

Performance of the required classification in a significantly reduced amount of time, in turn enabling real-time stress assessment including, as identified above, real-time assessment using wearable devices.

Extensive training data is used to achieve global usability of the systems and methods.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A reduced computation method of real-time classifying brain electroencephalograph (EEG) signals from a subject as indicative of the subject being in a state of mental stress or a state of no mental stress, consisting essentially of
    acquiring short windows of raw EEG signals from the subject and inputting the short windows to a computer that includes a processor coupled by a bus to a memory configured to store data and processor-executable instructions;
    filtering, by the computer according to processor-executable filtering instructions stored in the memory, the short windows of raw EEG signals to remove delta and gamma bands and retain alpha, beta, and theta signals, to produce filtered EEG signals;
    inputting the filtered EEG signal to a deep learning convolutional neural network (DLCNN) comprising gated recurring units (GRUs);
    performing a classifying, by the DLCNN, wherein the classifying comprises:
        i) GRUs of DLCNN extracting temporal features of the filtered EEG signals,
        and ii) GRUs of the DLCNN classifying the temporal features to obtain a classification result of mental stress or no mental stress, and, optionally:
    displaying, by a display device, one or both of the EEG signals and the classification result, and/or
    when the subject is in a state of mental stress, providing an anti-stress therapy to the subject;
    wherein the reduced computation method is performed in real time.

2. The reduced computation method of claim 1, wherein the DLCNN comprises at least one input layer, at least one fully connected layer, and at least one layer comprising GRUs, wherein the at least one layer comprising GRUs is located between an input layer and a fully connected layer.

3. The reduced computation method of claim 1, wherein: the acquiring short windows of raw EEG signals comprises a receiving, by a microcontroller that includes processing circuitry, which is secured to a wearable device that is worn by the subject, of the raw EEG signals obtained from the subject by an EEG sensor that is secured to the wearable device, or to another wearable device that is worn by the subject, and the extracting and the classifying are performed in real-time by the processing circuitry of the microcontroller.

4. The reduced computation method of claim 1, wherein the extracting and classifying are performed in real-time by processing circuitry embedded in a mobile device.

5. A reduced computation method of assessing mental stress in real time in a subject consisting essentially of filtering raw EEG signals to remove delta and gamma bands and retain alpha, beta, and theta bands, to produce filtered EEG signals;

transforming the filtered EEG signals into windows;

performing a classifying, by a deep learning convolutional neural network (DLCNN) comprising gated recurring units (GRUs), the classifying comprising:

i) extracting temporal features of the filtered EEG signals, and ii) classifying the temporal features to obtain a classification result of mental stress or no mental stress;

outputting a classification result in real time, and optionally, when a classification result of mental stress is obtained, providing the subject with a therapy to decrease mental stress.

6. The reduced computation method of claim 5, wherein the windows are less than 1 second.

7. The reduced computation method of claim 6, wherein the windows are less than 200 milliseconds.

8. The reduced computation method of claim 7, wherein the windows are 40 milliseconds.

9. A wearable device comprising processing circuitry configured to perform the reduced computation method of claim 5.

* * * * *

UNITED STATES PATENT AND TRADEMARK OFFICE
CERTIFICATE OF CORRECTION

| | |
|---|---|
| PATENT NO. | : 11,559,232 B1 |
| APPLICATION NO. | : 17/681790 |
| DATED | : January 24, 2023 |
| INVENTOR(S) | : Ubaid M. Al-Saggaf et al. |

It is certified that error appears in the above-identified patent and that said Letters Patent is hereby corrected as shown below:

In the Specification

Add the following just prior to the claims which begin at Column 14, Line 29 as follows:
STATEMENT OF ACKNOWLEDGEMENT
The authors extend their appreciation to the Deputyship for Research & Innovation, Ministry of Education in Saudi Arabia, for funding this research work through the project number (IFPRC-118-135-2020) and King Abdulaziz University, DSR, Jeddah, Saudi Arabia.

Signed and Sealed this
Sixth Day of August, 2024

Katherine Kelly Vidal
*Director of the United States Patent and Trademark Office*